(12) United States Patent
Boit et al.

(10) Patent No.: US 8,518,185 B2
(45) Date of Patent: Aug. 27, 2013

(54) GRANULATED MALTITOL FOR DIRECT COMPRESSION AND METHOD OF PREPARATION THEREOF

(75) Inventors: Baptiste Boit, Lestrem (FR); Pierrick Duflot, La Couture (FR); Jose Lis, La Gorgue (FR)

(73) Assignee: Roquette Freres, Lestrem (FR)

(*) Notice: Subject to any disclaimer, the term of this patent is extended or adjusted under 35 U.S.C. 154(b) by 0 days.

(21) Appl. No.: 13/529,063

(22) Filed: Jun. 21, 2012

(65) Prior Publication Data

US 2012/0259103 A1     Oct. 11, 2012

Related U.S. Application Data

(62) Division of application No. 12/341,689, filed on Dec. 22, 2008, now Pat. No. 8,232,388.

(30) Foreign Application Priority Data

Dec. 20, 2007  (FR) ..................... 07 60174

(51) Int. Cl.
*C13B 30/02*   (2011.01)
*C07H 1/06*    (2006.01)
*C07H 15/04*   (2006.01)

(52) U.S. Cl.
USPC .......... 127/60; 536/123.13; 536/127

(58) Field of Classification Search
USPC .............. 127/60; 536/123.13, 127
See application file for complete search history.

(56) References Cited

U.S. PATENT DOCUMENTS

| | | |
|---|---|---|
| 3,915,736 A | 10/1975 | Oyamada et al. |
| 3,918,986 A | 11/1975 | Hiraiwa |
| 4,248,895 A | 2/1981 | Stroz et al. |
| 4,408,041 A | 10/1983 | Hirao et al. |
| 4,831,129 A | 5/1989 | Serpelloni |
| 4,846,139 A | 7/1989 | Devos et al. |
| 4,849,023 A | 7/1989 | Devos et al. |
| 5,651,829 A | 7/1997 | Caboche |
| 6,120,612 A | 9/2000 | Mitsuhashi et al. |
| 6,863,737 B2 | 3/2005 | Ueno et al. |
| 2005/0118316 A1 | 6/2005 | Ueno et al. |

FOREIGN PATENT DOCUMENTS

| | | |
|---|---|---|
| EP | 0 185 595 | 6/1986 |
| EP | 0 189 704 | 8/1986 |
| EP | 0 220 103 | 4/1987 |
| EP | 0 561 585 | 9/1993 |
| EP | 0 735 042 | 10/1996 |
| EP | 1 300 414 | 4/2003 |
| FR | 2 588 005 | 4/1987 |
| GB | 1 383 724 | 2/1975 |
| JP | 48-61665 | 8/1973 |
| JP | 87619/74 | 8/1974 |
| JP | 110620/74 | 10/1974 |
| JP | 50-59312 | 5/1975 |
| JP | 50-129769 | 10/1975 |
| JP | 51-113813 | 10/1976 |
| JP | 57-47680 | 10/1982 |
| JP | 58-158145 | 9/1983 |
| WO | 2004/067595 | 8/2004 |
| WO | 2005/037849 | 4/2005 |

OTHER PUBLICATIONS

Definition of order, Oxford English Dictionary, http://www.oed.com/viewdictionaryentry/Entry/132334, accessed online on Dec. 6, 2012.*
"2.9.15. Volume Apparent", Pharmacopee Europeenne 5.0, Tome 1, pp. 256-257, EDQM, Conseil de I'Europe, Strasbourg, France, published 2004.
"2.9.16. Ecoulement", Pharmacopee Europeenne 5.0, Tome 1, pp. 257-258, EDQM, Conseil de I'Europe, Strasbourg, France, published 2004.
French Search Report, dated Jul. 25, 2008 and issued in corresponding French Patent Application No. 0760174.

* cited by examiner

*Primary Examiner* — Shaojia Anna Jiang
*Assistant Examiner* — Jonathan S Lau
(74) *Attorney, Agent, or Firm* — Young & Thompson

(57) ABSTRACT

Method of producing granulated maltitol, including the stages: preparing maltitol syrup having less than 50 wt.% dry matter and greater than 70 wt.% maltitol, introducing to a fluidized air bed granulator, a pulverulent bed of crystallized maltitol with a concentration at least equal to 99 wt.% and a mean diameter between 30 and 100 μm, controlling the air inlet temperature between 100 and 120° C. and air velocity between 1 and 2 m/s, fine spraying the maltitol syrup into the granulator, at between 35 and 45° C., onto the moving pulverulent bed; the bed being between 30 and 60° C.; the mass of the bed representing constantly at least 2.5 times the mass of the sprayed syrup, drying, after fine spraying, by raising the air temperature below the melting point of maltitol to obtain a bed temperature between 70 and 80° C., cooling the granulated maltitol to at most 25° C. and collecting.

19 Claims, No Drawings

GRANULATED MALTITOL FOR DIRECT COMPRESSION AND METHOD OF PREPARATION THEREOF

The present invention relates to a novel granulated maltitol of high purity, displaying excellent compressibility and low hygroscopicity.

It also relates to a particular method of obtaining said granulated maltitol and to its uses in the food and pharmaceutical industries.

4-O-alpha-D-glucopyranosyl-D-sorbitol, commonly called maltitol, is a polyol obtained industrially by hydrogenation of maltose. It is of considerable interest owing to the fact that it is more stable chemically and less calorific than sucrose, yet advantageously possesses organoleptic properties very similar to those of this sugar. Moreover, maltitol possesses the particular characteristic that it is not cariogenic, for which reason it has already found a variety of industrial applications, notably in the food and pharmaceutical industries.

For a very long time, maltitol was only marketed in the form of low-concentration syrups. This polyol is for example the main ingredient of the syrups LYCASIN® 80/55 and MALTISORB® 75/75, which have been marketed by the applicant for more than thirty years.

The maltitol contents of these syrups never exceed 78% of their dry matter.

Next, maltitol has been marketed in the form of amorphous, impure powders. Thus, maltitol solutions have often been spray-dried. According to statements in the literature, this technique has always been regarded as particularly difficult to apply on account of considerable adherence in the spraying towers but also owing to the very hygroscopic nature of the powders thus obtained.

A great many patents attest to the considerable efforts directed at overcoming these problems.

We may mention for example:
  patents GB 1 383 724, JP 49-87619 and U.S. Pat. No. 4,248,895, which propose adding to the maltitol solutions, before spraying, various substances such as alginates, celluloses, modified starches, polyvinylpyrrolidone, hydrophilic polymers, proteins or protein extracts, in order to reduce adherence in the spraying towers,
  patents JP 50-59312 and JP 51-113813, which describe methods of spraying anhydrous compositions of molten maltitol,
  patents JP 49-110620, U.S. Pat. Nos. 3,918,986; 3,915, 736, JP 50-129769 and JP 48-61665, which present methods for reducing the hygroscopicity of anhydrous maltitol powders, either by adding anticlumping substances, or by coating the maltitol powders with saccharides, polyols or fats, or by wet granulation.

It was only towards 1980 that maltitol crystals were produced for the first time. Before then, this polyol had always been regarded as a non-crystallizable product. This erroneous assumption, which had long been accepted, in fact arose from the fact that the crystallization of maltitol from a supersaturated solution is not as spontaneous as with other polyols such as mannitol, erythritol or isomalt for example. Certain characteristics that are peculiar to maltitol, in particular its viscosity and its solubility, probably led to the difficulties encountered.

To date, the only known crystalline form of maltitol is the anhydrous form, described in patent U.S. Pat. No. 4,408,041 of the company HAYASHIBARA.

A few years later, the first pseudo-crystalline powders of maltitol appeared on the market. These were, and still are, for some of them, prepared by a technique called "massing", consisting of causing a dehydrated solution of maltitol to set, having a concentration that can reach at best 90%, by adding a primer composed of crystals of sugars or of polyols.

Such a method is described for example in documents JP 57-47680 and JP 58-158145.

It was also proposed in patent U.S. Pat. No. 4,408,401 mentioned previously as well as in patent U.S. Pat. No. 6,120, 612, both held by the company HAYASHIBARA, to prepare pulverulent crystalline mixtures, called "total sugar", by spraying of pre-crystallized solutions or cooked masses.

The latter are obtained by very slow cooling of an aqueous solution supersaturated with maltitol, and additionally containing large amounts of other polyols such as sorbitol, maltotriitol and maltotetraitol and other polyols with higher degree of polymerization.

With very slow cooling and by adding a crystalline primer of maltitol, maltitol crystals are caused to appear and grow in the solution. When 25 to 60% of the maltitol in this aqueous solution has crystallized, spraying is then carried out at a very low temperature, that is, as indicated, at a temperature between 60 and 100° C. so as not to cause disappearance of the crystals that have been generated deliberately.

In this way, the "total sugar" obtained contains 25 to 60% of crystallized maltitol in the form of crystals completely identical to those obtained by crystallization in water.

Moreover, this "total sugar" is far from being sufficiently crystalline, since it is stated that it requires, according to the description and notably to Example 4, further drying, for about 40 minutes, as well as ageing for 10 hours.

It is understood that this method, which is very time-consuming, apparently has never been developed further.

A decisive step in the development of crystalline powders of maltitol of very high concentration was taken, owing to the work of the applicant, by the development of new methods of production based on the application of techniques of fractionation by continuous chromatography. These methods, the objects of patents EP 0 185 595 and EP 0 189 704, make it possible to obtain, at a competitive cost, powders with purity of up to 99%, simply by crystallization in water of the maltitol contained in a chromatographic fraction with a particularly high content of this polyol.

A crystalline powder of this kind has for example been marketed for several years by the applicant under the trade name crystallized MALTISORB®.

The techniques called "massing" on the one hand and crystallization in water on the other hand, are now almost the only methods used industrially. The products thus obtained, which are of very variable crystallinity, are especially suitable for certain applications such as chewing-gum or chocolate.

However, there are other applications where these products are not entirely satisfactory. This is the case for example when we wish to use maltitol to replace sucrose or lactose in dry pharmaceutical forms such as tablets and nutritive powder preparations for dilution.

For these particular applications, both for the pseudo-crystalline powders of maltitol obtained by the "massing" technique and for the crystalline powders of maltitol containing crystals obtained by crystallization of maltitol in water, it is found that the latter have one or more drawbacks, and in particular:
  they are poor excipients for compression,
  they are too hygroscopic and so are liable to bulking or clumping,
  they do not flow readily,
  they only dissolve very slowly in water, or they do not meet the criteria for identification and purity stipulated by various pharmacopoeias.

However, it has already been proposed, in the case of maltitol, to use extrusion to improve its capacity for compression. Such a method is described for example in patents EP 0 561 585, EP 1 300 414, and in patent EP 0 220 103 which is owned by the applicant.

This method is not ideal, however, because unfortunately it is unable to improve all of the drawbacks noted above for the products on the market.

Desiring to improve on the prior art, the applicant therefore tried to develop a granulated maltitol without the drawbacks relating to compression, hygroscopicity and therefore clumping, flow or dissolution that characterize the known maltitol powders.

Certainly it might have been thought that the identified need could be satisfied by other polyols. It is found that this is not so, as none of them possesses characteristics of solubility, hygroscopicity, sugary taste and melting as close to sucrose as are provided by maltitol.

After conducting extensive research on this subject, the applicant succeeded in preparing granulated maltitol that does not have the drawbacks found with the known maltitols.

Accordingly, the invention relates, firstly, to a granulated maltitol with high maltitol concentration, i.e. greater than or equal to 97%, preferably between 98 and 99%, characterized in that it has:
 water content less than 1%, preferably less than 0.5%, more preferably less than or equal to 0.4%,
 compressibility greater than or equal to 300 N, preferably between 300 and 500 N,
 hygroscopicity less than or equal to 2.5%, preferably between 1 and 2%.

The concept of concentration must be understood, in the sense of the present invention, as corresponding to the percentage of maltitol expressed in dry/dry weight relative to all of the carbohydrates present in the crystalline composition of maltitol.

These carbohydrates can be sugars such as in particular sorbitol, maltotriitol and polyols of higher DP (degree of polymerization).

Said concentration is measured by high-performance liquid chromatography.

The granulated maltitol according to the invention is firstly characterized by a water content, determined after heating in a stove at 130° C. for 2 hours, less than 1%, preferably less than 0.5% and more preferably less than or equal to 0.4%.

It is quite remarkable that a granulated maltitol should have, for such a high concentration of maltitol, such a low water content.

As an example, among the granulated maltitols of the prior art, that described more particularly in international patent application WO 2004/067 595 and called "customized sweetener 1" (obtained by a stage of spraying of a mixture of maltitol syrup on a bed of crystals of this same polyol) has a water content that cannot be less than 1% (the water content of such granules is said to be between 1 and 7%, preferably between 1 and 5% and more preferably between 1 and 3%).

In order to offer maltitol granules with water content less than 3%, preferably between 0.5 and 1.5%, it is recommended in said international patent application WO 2004/067 595 to add 5 to 50 wt. % of hydrogenated starch hydrolysates (HSH) to the maltitol granules "customized sweetener 1" and thus obtain "customized sweetener 2".

The maltitol granules thus obtained cannot in this case boast of a high maltitol concentration like those of the invention.

Moreover, it is only by this addition of HSH that the granulated maltitols of said international patent application WO 2004/067 595 display satisfactory flow.

The granulated maltitol according to the invention possesses, moreover, very good capacity for being compressed for preparing tablets that are to be chewed or sucked and very good capacity for being mixed with other products.

The compressibility of the granulated maltitol is determined as follows.

We measure the force, expressed in newtons, that is required to crush a tablet prepared by means of an alternative laboratory press FROGERAIS AM from said maltitol lubricated with 1% of magnesium stearate (lubrication being achieved by mixing granulated maltitol and magnesium stearate in a TURBULA T2C mixer for 5 minutes), therefore reflecting the crushing strength of the tablet, which is cylindrical with convex faces (radius of curvature of 13 mm), with a diameter of 13 mm, thickness of 6 mm and weight of 0.857 g, i.e. has an apparent density of 1.5 g/ml. This force, expressing the hardness, is measured on an ERWEKA TBH 30 GMD hardness tester. The value given in newtons corresponds to a mean value from 10 measurements.

The granulated maltitol according to the invention has a compressibility greater than or equal to 300 N, preferably between 300 and 500 N.

Owing to this remarkable compressibility value, the mechanical strength of the tablets obtained with said granulated maltitol according to the invention is very high, relative to that of tablets obtained with the products manufactured by crystallization in water, by extrusion and by spraying.

As a first example, the applicant found that the granulated maltitol described in patent application WO 2005/037 849 had a compressibility well below that of the granulated maltitol according to the invention.

In addition, this compressibility is obtained between 35 and 45 kN, the maximum admissible force for such a tablet size before breaking of the tableting equipment.

As a second example, if the crystalline compositions of maltitol described by the applicant in their patent EP 735 042 have a compressibility equivalent to that of the granulated maltitol according to the invention when the measurements are carried out on tablets with a density of 1.35 g/ml (measurement conditions stated in said patent EP 0 735 042), they do not allow tablets to be obtained that resist crushing when the density of the tablets reaches a value of 1.5 g/ml (density value stipulated by the compressibility test used for testing the crushing strength of the granulated maltitol according to the invention).

The granulated maltitol according to the invention thus displays remarkable and exceptional compressibility.

The granulated maltitol of the invention is also characterized by its hygroscopicity.

It displays hygroscopicity, determined from its weight variation between 0 and 86% of relative humidity (RH), less than or equal to 2.5%, preferably between 0.15 and 2.5% and more preferably between 1 and 2%.

The test for measuring hygroscopicity consists here of evaluating the weight variation of the sample of maltitol when it is submitted to varying RH at 20° C. in an instrument made by the company SURFACE MEASUREMENT SYSTEMS (London UK) and designated Dynamic Vapour Sorption Series 1.

This instrument consists of a differential microbalance, with which it is possible to quantify the weight variation of a sample relative to a reference (here the reference pan of the differential balance is empty) when submitted to different climatic conditions.

The carrier gas is nitrogen, and the weight of the sample is between 10 and 12 mg. The programmed RH values are 0% RH for 500 minutes (dehydration) then 20, 40, 60, 70, 75, 80, 82, 84, 86% RH. The stability factor, permitting automatic passage from one RH to the next, is the ratio dm/dt, which is set at 0.002%/min for 20 minutes.

Finally, a table of values is obtained corresponding for each RH to the equation $[(m-m_0)/m_0] \times 100$ where "m" is the mass of the sample at the end of testing for the RH in question and "$m_0$" is the mass at the end of dehydration.

The results are expressed as the difference between the values of weight variation (as described above) obtained at 86% and after dehydration (at 0% RH), respectively.

The granulated maltitol according to the invention thus has hygroscopicity of less than or equal to 2.5%, preferably between 1 and 2%.

Relative to the hygroscopicity value of the crystalline compositions of maltitol notably described by the applicant in their patent EP 0 735 042, it is found that the value is higher for the granulated maltitol according to the invention.

However, this value is still low, and entirely acceptable, in view of the remarkable compressibility of the granulated maltitol according to the invention.

According to a preferred variant, the granulated maltitol according to the invention can, moreover, also be characterized by its apparent density and its flowability.

The apparent density of the granulated maltitol according to the invention is determined according to the method of measurement recommended by the European Pharmacopoeia (Ph.Eur. 5.0 Vol. 1, 01/2005: 20915 paragraph 2.9.15 APPARENT VOLUME; equipment according to FIG. 2-9-15-1).

In these conditions, the granulated maltitol according to the invention advantageously has an apparent density between 0.30 and 0.90 g/ml, preferably between 0.40 and 0.80 g/ml.

As for the free flow of the granulated maltitol according to the invention, it is also determined according to the method of measurement recommended by the European Pharmacopoeia (Ph.Eur. 5.0 Vol. 1, 01/2005: 20916, paragraph 2.9.16 FLOW; equipment according to FIG. 2.9.16-2).

The granulated maltitol of the invention then advantageously has a free flow between 5 and 12 seconds, preferably between 6 and 9 seconds.

This value is entirely satisfactory, relative to those of the maltitol powders of the prior art, as will be illustrated below.

Another functional property of the granulated maltitol according to the invention is that of dissolving rapidly in water.

To measure this rate of dissolution, exactly 5 g of the test product is put in 150 g of degassed and demineralized water, held at 20° C. and stirred at 200 rev/min in a 250-ml squat beaker. The dissolution time corresponds to the time taken, after introduction of the product, to obtain perfect visual clarity of the preparation.

In these conditions, the granulated maltitol according to the invention can notably have a rate of dissolution less than or equal to 40 seconds and preferably less than or equal to 35 seconds and more preferably less than or equal to 30 seconds.

The granulated maltitol according to the invention can finally, according to another variant, also be characterized by its mean volumetric diameter (arithmetic mean) D4.3.

These values are determined on a LASER diffraction granulometer type LS 230 from the company BECKMAN-COULTER, equipped with its powder dispersion module (dry method), following the manufacturer's technical manual and specifications.

The measurement range of the LASER diffraction granulometer type LS 230 is from 0.04 µm to 2000 µm. The operating conditions of hopper screw speed and intensity of vibration of the dispersion channel are determined in such a way that the optical concentration is between 4% and 12%, ideally 8%.

The results are calculated in percentage by volume, and expressed in µm.

The granulated maltitol according to the invention thus has a mean volumetric diameter between 200 and 500 µm, preferably between 250 and 400 µm.

The granulated maltitol according to the invention can be obtained by carrying out the spraying of a syrup relatively rich in maltitol relative to the amount of carbohydrates present in said syrup (maltitol concentration at least equal to 70 wt. %), on a moving pulverulent bed of particles of crystallized maltitol of high purity (maltitol concentration at least equal to 99 wt. %).

The granulated maltitol according to the invention can in particular be obtained by applying the method in a granulator, said method comprising the following stages:

a) preparing a maltitol syrup having a dry matter less than 50 wt. %, preferably between 20 and 45 wt. %, and with a maltitol concentration greater than 70 wt. %, preferably between 75 and 95 wt. %, b) introducing, in a fluidized air bed granulator, a pulverulent bed of crystallized maltitol with a concentration at least equal to 99 wt. % and having a mean diameter between 30 and 100 µm, c) controlling the air inlet temperature of the granulator to a value between 100 and 120° C., and the velocity of the fluidization air to a value between 1 and 2 m/s, d) fine spraying of the maltitol syrup from stage a) in said granulator, at a temperature between 35 and 45° C., preferably at a temperature of the order of 40° C. on the pulverulent moving bed of particles of crystallized maltitol of stage b); said bed having a temperature between 30 and 60° C.; the mass of the bed representing constantly at least 2.5 times the mass of the sprayed syrup, e) drying by raising the temperature of the air of the granulator, at the end of fine spraying of said syrup, to a temperature less than the melting point of maltitol, preferably to a temperature less than 130° C., more preferably to a temperature of the order of 120° C., until the temperature of the bed is between 70 and 80° C., preferably of the order of 75 ° C., f) cooling of the granulated maltitol thus obtained to a temperature of at most 25° C., preferably to a temperature of the order of 20° C. and collecting of the granulated maltitol thus obtained.

Stage (a) of the method according to the invention comprises preparing a maltitol syrup having a dry matter of less than 50 wt. %, preferably between 20 and 45 wt. %, and having a maltitol concentration greater than 70 wt. %, preferably between 75 and 95 wt. %.

Such a syrup can advantageously be prepared starting from MALTISORB® 75/75 that is marketed by the applicant, characterized by a dry matter of 75% and a maltitol concentration of 75% (notably with 1.5% of sorbitol and 12.5% of polyols having a degree of polymerization of 3-DP3H).

Preferably, in the maltitol syrup of stage (a) which will be sprayed in the granulator, it is possible to add crystalline maltitol having the same maltitol concentrations as those of the crystallized maltitol that will be fed into the granulator in stage (b).

This mixture of maltitol syrup and of crystallized maltitol makes it possible to adjust the dry matter of the maltitol syrup to be sprayed, which will have the effect, as will be illustrated below, of modulating the granulometry, density and maltitol concentration of the granulated maltitol according to the invention.

Stage (b) of the method according to the invention comprises feed, into a fluidized air bed granulator, of crystallized maltitol of concentration at least equal to 99 wt. % and having a mean diameter between 30 and 100 μm.

The applicant recommends using crystallized maltitol of the type that it markets under the trade names MALTISORB® P35 or MALTISORB® P90 (the number written next to the letter P showing the mean diameter of the crystallized maltitol expressed in μm).

Stage (c) of the method according to the invention comprises controlling the air inlet temperature of the granulator to a value between 100 and 120° C., and the velocity of the fluidization air to a value between 1 and 2 m/s.

The motion of the particles constituting the pulverulent bed is thus achieved by fluidization in the air.

These conditions of temperature and of inlet air flow rate are advantageously selected so as to ensure optimum mixing of the sprayed maltitol syrup on the moving bed of particles of crystalline maltitol in the granulator.

Stage (d) of the method according to the invention comprises carrying out fine spraying of the maltitol syrup from stage (a) at a temperature between 35 and 45° C., preferably at a temperature of the order of 40° C. on a pulverulent moving bed of particles of crystallized maltitol of concentration at least equal to 99 wt. %; the flow rate in spraying being controlled so that said bed has a temperature between 30 and 60° C.; the mass of the bed constantly representing at least 2.5 times the mass of the sprayed syrup.

It is preferable to avoid coarse spraying of the syrup, as in that case we observe adherence, poor distribution of the syrup and of the grain size of the final product.

Also, for the granulated maltitol according to the invention to have the specific properties described above, it is advisable to use equipment that can form very fines droplets, or even a mist, from the syrup.

The flow rate in spraying must be controlled, by any method known by a person skilled in the art, so as to obtain a temperature in the bed between 30 and 60° C.

Stage (e) of the method according to the invention comprises carrying out drying of the granulated maltitol by raising the temperature of the air of the granulator at the end of fine spraying of said syrup to a temperature less than the melting point of maltitol, preferably to a temperature less than 130° C., more preferably to a temperature of the order of 120° C., until the temperature of the bed is between 70 and 80° C., preferably of the order of 75° C.

Stage (f) of the method according to the invention comprises cooling the granulated maltitol thus obtained to a temperature of at most 25° C., preferably to a temperature of the order of 20° C. and finally, collecting the granulated maltitol thus obtained.

Advantageously, it is possible to have an additional stage of sieving, as will be illustrated below.

The final water content of the granulated maltitol after drying, cooling and collection is less than 1%, preferably less than 0.5% and more preferably less than or equal to 0.4%.

The applicant has demonstrated that the granulated maltitol could be manufactured advantageously, for example using a granulator of type GLATT AGT 400, which makes it possible, owing to its design, to adapt and apply all the essential stages of the method according to the invention.

With this equipment it is in fact possible to achieve very fine spraying, by means of its two-fluid nozzle, of a syrup having a temperature between 35 and 45° C. and a dry matter less than 50 wt. %, preferably between 20 and 45 wt. %, on a bed of maltitol particles, fluidized with air. The mass of maltitol particles of the bed represents at least 2.5 times the mass of the syrup sprayed, preferably 8 to 2.5 times, more preferably 6 to 3 times the mass of the syrup sprayed.

The granulated maltitol according to the invention can advantageously be used as sweetener, filler or texturizing agent, excipient or support of various additives.

It is particularly recommended, by virtue of its specific properties, for the manufacture of tablets and of dissolving powders in the food and pharmaceutical areas.

However, there is nothing to stop it being used for any other purpose, for example for formulating chewing-gums, syrups or sweets.

The invention will be understood even better from the examples that follow, which are not intended to be limiting and merely present certain embodiments and certain advantageous properties of the granulated maltitol according to the invention.

Example 1

Preparation of granulated maltitol according to the invention and comparison with the products of the prior art.

25 kg of crystalline maltitol marketed by the applicant under the trade name MALTISORB® P90 is put in a GLATT AGT 400 granulator operating in batch mode (the outlet of the air classifier is closed).

The inlet air flow rate is set at 800 m³/h with a temperature of 100° C. (so as to obtain a velocity of the fluidization air at a value between 1 and 2 m/s).

A syrup, consisting of 1.7 kg of MALTISORB® 75/75 diluted with 3 kg of water, is sprayed at a temperature of 40° C. by means of a two-fluid nozzle (air pressure of 4 bar) in "bottom spray" position on the maltitol particles in motion in the air stream.

The flow rate in spraying is controlled so as to obtain a temperature in the moving bed of particles of 31° C. At the end of spraying, the temperature of the air is increased to 120° C. These conditions are maintained until the temperature in the bed of powder rises to 75° C.

The powder is cooled to 20° C. and then sieved between 100 and 500 μm.

The granulated maltitol obtained will be given the reference (A) in the rest of this Example 1.

Two other granulated maltitols according to the invention are prepared by a method similar to that described above to obtain the granulated maltitol (A), except that:
  the first granulated maltitol with reference (B) is prepared from 25 kg of crystalline maltitol marketed by the applicant under the trade name MALTISORB® P35, for spraying, by means of a nozzle in "top spray" position, 2.5 kg of MALTISORB® 75/75 diluted with 3 kg of water,
  the second granulated maltitol with reference (C) is prepared from 25 kg of crystalline maltitol marketed by the applicant under the trade name MALTISORB® P35, for spraying, by means of a nozzle in "top spray" position, 1.8 kg of MALTISORB® 75/75 diluted with 5 kg of water.

Moreover, for preparation of these two batches (B) and (C), crystalline maltitol is added to the maltitol syrup in order to increase its dry matter.

Table I below presents some of the process variables for manufacture of the granulated maltitols (A), (B) and (C).

TABLE I

|  | Manufacture of granulated maltitol (A) | Manufacture of granulated maltitol (B) | Manufacture of granulated maltitol (C) |
| --- | --- | --- | --- |
| Type of crystalline maltitol | MALTISORB ® P90 | MALTISORB ® P35 | MALTISORB ® P35 |
| Amount (kg) | 25 | 25 | 25 |
| Amount of MALTISORB ® 75/75 (kg) | 1.7 | 2.5 | 1.8 |
| Water (kg) | 3 | 3 | 5 |
| Amount of MALTISORB ® P90 added to the syrup (kg) | 0 | 1 | 2 |
| Dry matter of the syrup (%) | 27 | 44 | 38 |
| Concentration of maltitol syrup (%) | 75 | 83 | 90 |
| Type of spraying | "bottom spray" | "top spray" | "top spray" |
| Nozzle air pressure (bar) | 4 | 3 | 3 |
| Air flow rate (m³/h) | 800 | 600 | 550 |
| Air temperature during spraying (° C.) | 100 | 115 | 113 |
| Temperature of drying air (° C.) | 120 | 120 | 120 |
| Temperature in the bed during spraying (° C.) | 31 | 55 | 50 |
| Bed temperature at end of spraying (° C.) | 75 | 80 | 75 |
| Sieving (μm) | 100-500 | 100-800 | 100-800 |

The principal functional characteristics of the granulated maltitols (A), (B) and (C) are presented in Table II below. A first comparative study is carried out between the maltitols (A), (B) and (C) and a prior art composition with a maltitol concentration of less than 96%. This maltitol, referred to below as maltitol (H), is obtained in accordance with patent WO 2005/037849.

TABLE II

|  | (A) | (B) | (C) | (H) |
| --- | --- | --- | --- | --- |
| Maltitol concentration (%) | 98.3 | 97.8 | 98.3 | 95.2 |
| Water content (%) | 0.35 | 0.4 | 0.35 | 0.48 |
| Compressibility (N) | 332 | 354 | 321 | 220 |
| Hygroscopicity (%) | 1.54 | 1.72 | 1.17 | 6.72 |
| Apparent density (g/ml) | 0.67 | 0.48 | 0.48 | 0.71 |
| Flow (s) | 6 | 11 | 9 | 4 |

In addition to a maltitol concentration much lower than that of the powdered maltitols (A), (B) and (C), the prior art maltitol (H) has a very strong hygroscopicity that may be up to 6 times greater than that of the maltitol according to the invention. Such a hygroscopicity is responsible for an instability of the powders and of the derived products, due to a high water uptake. Clumping or setting of the powders or loss of their flow characteristic are, for example, observed. These phenomena are not observed for the powders having hygroscopicity characteristics in accordance with those of the maltitol according to the invention.

A second comparative study, carried out using prior art compositions very rich in maltitol, is given in Table III, compared with the granulated maltitols (A), (B) and (C) in accordance with the invention. These various prior art maltitols are the following:

- a crystalline powder containing maltitol crystals obtained by crystallization in water (MALTISORB® P 200)—compound (D);
- a powder obtained according to the "massing" technique—compound (E);
- a maltitol powder, extruded according to the conditions stated in patent EP 0 220 103—compound (F),
- a crystalline composition of maltitol obtained by spraying according to the conditions stated in patent EP 0 735 042—compound (G).

In order to compare the functional properties of the granulated maltitols of the invention relative to maltitols or crystalline compositions of maltitol of the prior art, the flowability and the apparent densities given in this table were measured by the methods described in patent EP 0 735 042:

- the flowability of the granulated maltitol according to the invention is determined using an instrument marketed by the company HOSOKAWA under the trade name "Powder Tester" by applying the method for calculating a flow index that is also called "flowability" described in the articles of CARR R. L. in Chem. Eng. 72, No. 1, 163-168 (1965) and in Chem. Eng. 72, No. 2, 69-73 (1965). The granulated maltitol of the invention has a flow index between 70 and 85.
- the apparent density is measured using an instrument marketed by the company HOSOKAWA under the trade name "Powder Tester" by applying the method recommended for measuring non-tamped density. In these conditions, the granulated maltitol according to the invention has an apparent density between 0.40 g/ml and 0.80 g/ml, preferably between 0.42 and 0.75 g/ml.

The other measurements are carried out according to the methods recommended in the present patent application.

TABLE III

|  | (A) | (B) | (C) | (D) | (E) | (F) | (G) |
|---|---|---|---|---|---|---|---|
| Maltitol concentration (%) | 98.3 | 97.8 | 98.3 | 99.8 | 96.2 | 98 | 99.8 |
| Water content (%) | 0.35 | 0.4 | 0.35 | 0.2 | 0.7 | 0.2 | 0.3 |
| Compressibility (N) for tablets of density 1.35 g/ml | 142 | 156 | 158 | Measurement Impossible | Impossible to compress in this case | 140 | 135 |
| Compressibility (N) for tablets of density 1.5 g/ml | 332 | 354 | 321 | Measurement Impossible | Impossible to compress in this case | No measurement possible Splitting of the tablet | No measurement possible Splitting of the tablet |
| Hygroscopicity (%) | 1.54 | 1.72 | 1.17 | 0.13 | 3.94 | 2.1 | 0.24 |
| Apparent density (g/ml) measured according to EP 0 735 042 | 0.7 | 0.53 | 0.48 | 0.86 | 0.335 | 0.78 | 0.645 |
| Carr flow index measured according to EP 0 735 042 | 80 | 80 | 74.5 | 78 | 28.5 | 79 | 83 |
| Rate of dissolution (s) | 40 | 25-30 | 20-25 | 68 | 40 | 34 | 25 |
| Mean volumetric diameter (μm) | 289 | 357 | 330 | 200 | <100 μm | 580 | 250 |

In contrast to the crystalline compositions of maltitol of the prior art, the granulated maltitols according to the invention advantageously combine properties that have never been obtained simultaneously until now.

They in fact possess, at the same time, the characteristics of being compressible and of having low hygroscopicity, yet they flow easily and dissolve very quickly in water.

Example 2

Chewing-gums are prepared starting from the granulated maltitols (A), (B) and (C) of Example 1 according to the formulations given below (Table IV). For comparison, chewing-gums are also prepared with compound (E) from Example 1 and with a powder also obtained according to the so-called "massing" technique, but of higher granulometry—compound (H).

TABLE IV

|  | Formulation (1) | Formulation (2) | Formulation (3) | Formulation (4) | Formulation (5) |
|---|---|---|---|---|---|
| Gum base SUNCOM T (company CAFOSA) | 36 | 36 | 36 | 36 | 36 |
| Compound (H) | 28 | — | — | — | — |
| Compound (E) | — | 28 | — | — | — |
| Compound (A) | — | — | 28 | — | — |
| Compound (B) | — | — | — | 28 | — |
| Compound (C) | — | — | — | — | 28 |

TABLE IV-continued

|  | Formulation (1) | Formulation (2) | Formulation (3) | Formulation (4) | Formulation (5) |
|---|---|---|---|---|---|
| Crystallized xylitol marketed by the applicant under the trade name XYLISORB ® 90 | 34.3 | 34.3 | 34.3 | 34.3 | 34.3 |
| Flavour: "Mint flavour Fresh Peppermint Mane E0225511" | 1.5 | 1.5 | 1.5 | 1.5 | 1.5 |
| Aspartame | 0.2 | 0.2 | 0.2 | 0.2 | 0.2 |
| Total | 100.0 | 100.0 | 100.0 | 100.0 | 100.0 |

The texture of the sugar-free chewing-gums obtained in strictly identical conditions is measured and compared.

The texture of the chewing-gums is measured by penetrometry with the INSTRON 4502 universal tester marketed by the company INSTRON with the following protocol:
- use the 100 N measuring cell, and a cylindrical metal punch with diameter 3.9 mm
- measurement carried out on a sample of chewing-gum 30 mm long, 18 mm wide, 5 mm thick
- penetration at a speed of 50 mm/min.

The force is recorded in newtons, and the value obtained is the maximum force, knowing that the evaluation stops when there is a drop of 0.1N in the measured force.

The hardness of the chewing-gum is characterized during cooling (45° C., 35° C., 20° C.) and then during storage after 1 day, 8 days and 15 days at 50% RH and 20° C.

The results are summarized in Table V below:

| Hardness (N) | Formulation (1) | Formulation (2) | Formulation (3) | Formulation (4) | Formulation (5) |
|---|---|---|---|---|---|
| D0-45° C. | 1.3 | 1.8 | 1.4 | 1.5 | 1.5 |
| D0-35° C. | 2.5 | 3.5 | 2.6 | 2.9 | 2.9 |
| D0-20° C. | 7.6 | 10.9 | 6.8 | 9.4 | 10.2 |
| D + 1 at 50% RH/20° C. | 8.0 | — | 9.7 | 12.2 | 11.3 |
| D + 8 at 50% RH/20° C. | 8.3 | 12.4 | 9.2 | 11.3 | 9.7 |
| D + 15 at 50% RH/20° C. | 9.1 | 11.9 | 9.6 | 11.6 | 11.9 |

It is found that the chewing-gums based on granulated maltitol according to the invention are slightly harder than those prepared starting from compound (H) after 1 day of storage, but that the hardness values for the stabilized products (after 15 days) are very similar. The final texture of the chewing-gum is therefore similar.

None of the chewing-gums presented above produces a sandy or granular sensation in the mouth. The granulated maltitols according to the invention can therefore be used as such in chewing-gum, without requiring special grinding.

These analyses confirm the advantages offered by the granulated maltitol according to the invention in the formulation of chewing-gum when we wish to adjust its texture.

The invention claimed is:

1. A method of production of granulated maltitol, comprising the following stages:
   a) preparing a maltitol syrup having a dry matter less than 50 wt. %, and with a maltitol concentration greater than 70 wt. % of the carbohydrates of said syrup,
   b) introducing, in a fluidized air bed granulator, a pulverulent bed of crystallized maltitol with a concentration at least equal to 99 wt. % and having a mean diameter between 30 and 100 μm,
   c) controlling the air inlet temperature of the granulator to a value between 100 and 120° C., and the velocity of the fluidization air to a value between 1 and 2 m/s,
   d) fine spraying of the maltitol syrup from stage a) in said granulator, at a temperature between 35 and 45° C., on the pulverulent moving bed of particles of crystallized maltitol of stage b); said bed having a temperature between 30 and 60° C.; the mass of the bed representing constantly at least 2.5 times the mass of the sprayed syrup,
   e) drying by raising the temperature of the air of the granulator, at the end of fine spraying of said syrup, to a temperature less than the melting point of maltitol until the temperature of the bed is between 70 and 80° C.,
   f) cooling of the granulated maltitol thus obtained to a temperature of at most 25° C. and collecting the granulated maltitol thus obtained.

2. The method of claim 1, wherein the maltitol syrup in step a) has a dry matter between 20 and 45 wt.%.

3. The method of claim 1, wherein the maltitol concentration of the maltitol syrup in stage a) is between 75 and 95 wt. % of the carbohydrates of said syrup.

4. The method of claim 1, wherein the fine spraying of the maltitol syrup in stage d) is carried out at a temperature 40° C.

5. The method of claim 1, wherein the temperature of the air of the granulator in stage e) is raised to a temperature less than 130° C.

6. The method of claim 5, wherein the temperature of the air of the granulator in stage e) is raised to a temperature of 120° C.

7. The method of claim 1, wherein the temperature of the bed in stage e) is 75° C.

8. The method of claim 1, wherein the granulated maltitol is cooled to a temperature of 20° C. in stage f).

9. The method of claim 1, wherein the granulated maltitol is of concentration greater than or equal to 97% and has
   water content less than 1%,
   compressibility greater than or equal to 300 N, said compressibility being equal to the force required to crush a tablet prepared from the granulated maltitol lubricated with 1% of magnesium stearate and having an apparent density of 1.5g/mL,
   hygroscopicity less than or equal to 2.5%.

10. The method of claim 9, wherein the granulated maltitol has an apparent density, determined according to the method of measurement recommended by the European Pharmacopoeia (Ph. Eur. 5.0 Vol. 1, 01/2005; 20915 paragraph 2.9.15 APPARENT VOLUME; equipment according to FIG. 2.9.15-1), between 0.30 and 0.90 g/ml.

11. The method of claim 9, wherein the granulated maltitol has free flow, determined according to the method of measurement recommended by the European Pharmacopoeia (Ph. Eur. 5.0 Vol. 1, 01/2005; 20916 paragraph 2.9.16 APPARENT FLOW; equipment according to FIG. 2.9.16-2), of between 5 and 12 seconds.

12. The method of claim 9, wherein the granulated maltitol has a rate of dissolution in water less than or equal to 40 seconds, said rate of dissolution being the time taken, after introduction of 5 g of granulated maltitol in 150 g of degassed and demineralised water at 20° C. and stirred at 200 rev/min in a 250-ml squat beaker, to obtain perfect visual clarity of the resulting solution.

13. The method of claim 9, wherein the granulated maltitol has a mean volumetric diameter measured by LASER diffraction granulometry by means of a dry method module, between 200 and 500 μm.

14. The method of claim 9, wherein the granulated maltitol has a maltitol concentration between 98 and 99%.

15. The method of claim 9, wherein the granulated maltitol has
   water content less than 0.5%,
   compressibility between 300 and 500 N,
   hygroscopicity between 0.15 and 2.5%.

16. The method of claim 9, wherein the granulated maltitol has an apparent density, determined according to the method of measurement recommended by the European Pharmacopoeia (Ph. Eur. 5.0 Vol. 1, 01/2005; 20915 paragraph 2.9.15 APPARENT VOLUME; equipment according to FIG. 2.9.15-1), between 0.40 and 0.80 g/ml.

17. The method of claim 9, wherein the granulated maltitol has a rate of dissolution in water less than or equal to 35 seconds, said rate of dissolution being the time taken, after introduction of 5 g of granulated maltitol in 150 g of degassed and demineralised water at 20° C. and stirred at 200 rev/min in a 250-ml squat beaker, to obtain perfect visual clarity of the resulting solution.

18. The method of claim 9, wherein the granulated maltitol has a rate of dissolution in water less than or equal to 30 seconds, said rate of dissolution being the time taken, after introduction of 5 g of granulated maltitol in 150 g of degassed and demineralised water at 20° C. and stirred at 200 rev/min in a 250-ml squat beaker, to obtain perfect visual clarity of the resulting solution.

19. The method of claim 9, wherein the granulated maltitol has a mean volumetric diameter measured by LASER diffraction granulometry by means of a dry method module, between 250 and 400 μm.

* * * * *